United States Patent
Girard et al.

(10) Patent No.: US 6,442,736 B1
(45) Date of Patent: Aug. 27, 2002

(54) SEMICONDUCTOR PROCESSING SYSTEM AND METHOD FOR CONTROLLING MOISTURE LEVEL THEREIN

(75) Inventors: Jean-Marc Girard, Paris; Benjamin J. Jurcik, Saint Remy les Chevreuses; Jean Friedt, Neuilly-sur-Seine, all of (FR); James J. F. McAndrew, Lockport, IL (US)

(73) Assignees: L'Air Liquide Societe Anonyme A Directoire et Conseil de Surveillance pour l'Etude et l'Expolitation des Procedes Georges Claude, Paris (FR); American Air Liquide Inc., Fremont, CA (US)

( * ) Notice: Subject to any disclaimer, the term of this patent is extended or adjusted under 35 U.S.C. 154(b) by 0 days.

(21) Appl. No.: 09/677,885

(22) Filed: Oct. 3, 2000

(51) Int. Cl.$^7$ .................................. H01L 21/00
(52) U.S. Cl. ................................ 716/4; 438/16
(58) Field of Search ................ 438/16, 14–15, 438/17–18, 5–13, 800; 716/4, 5–6; 356/437

(56) References Cited

U.S. PATENT DOCUMENTS

| | | |
|---|---|---|
| 3,524,066 A | 8/1970 | Blakkan |
| 4,812,665 A | 3/1989 | Puumalainen et al. |
| 4,934,816 A | 6/1990 | Silver et al. |

(List continued on next page.)

FOREIGN PATENT DOCUMENTS

| | | |
|---|---|---|
| DE | 25 04 300 | 11/1975 |
| DE | DD144708 A | 9/1980 |
| DE | 3633931 | 4/1988 |
| DE | 4214840 | 11/1993 |
| EP | 0015170 | 9/1980 |
| EP | 0647845 | 4/1995 |
| EP | 0706042 | 4/1996 |
| EP | 0738887 | 4/1996 |
| GB | 2075213 | 11/1981 |
| GB | 2165640 | 4/1986 |
| WO | WO90/00732 | 1/1990 |
| WO | WO94/24528 | 10/1994 |

OTHER PUBLICATIONS

Kaur et al, "Multipass cell for molecular beam absorption spectroscopy," Applied Optics, Jan. 1, 1990, vol. 29, No. 1, pp. 119–124.

Stabb, "Industrielle Gasanalyse Industrial Gas Analysis," Technisches Messen, vol. 61, No. 3, Mar. 1, 1994, pp. 133–137.

White, "Long Optical Paths of Large Aperture," *J. Opt. Soc. Am.*, vol. 32 (1942), pp. 285–288.

Wilson, "Modulation Broadening of NMR and ESR Line Shapes," *J. Appn. Phys.*, vol. 34, No. 11, pp. 3276–3285 (1963).

T.A. Hu et al, "Improved Multipass Optics for Diode Laser Spectroscopy", *Review of Scientific Instuments*, vol. 64, No. 12, Dec. 1993, pp. 3380–3383.

Patent Abstracts of Japan, vol. 6, No. 59, JP 57–1953, Jan. 1982.

Smoak, Jr. et al., "Gas Control Improves EPI Yield," *Semiconductor Int'l.*, pp. 87–92 (1990).

(List continued on next page.)

*Primary Examiner*—Craig Thompson (57) ABSTRACT

Provided is a novel semiconductor processing system. The system includes a process chamber for treating a semiconductor substrate with one or more process gases comprising water vapor, means for delivering the water vapor or one or more precursors thereof to the process chamber, an exhaust conduit connected to the process chamber, an absorption spectroscopy system for sensing water vapor in a sample region, and a control system which controls water vapor content in the process chamber. Also provided is a method for controlling the water vapor level in a semiconductor process chamber. The system and method allow for measurement and control of the water vapor level in a semiconductor processing chamber in which water vapor is present as a process gas.

38 Claims, 6 Drawing Sheets

U.S. PATENT DOCUMENTS

| | | |
|---|---|---|
| 4,937,461 A | 6/1990 | Traina |
| 4,990,780 A | 2/1991 | Lee et al. |
| 5,045,703 A | 9/1991 | Wieboldt et al. |
| 5,047,639 A | 9/1991 | Wong |
| 5,065,025 A | 11/1991 | Doyle |
| 5,173,479 A | 12/1992 | Tell et al. |
| 5,220,402 A | 6/1993 | Harvey |
| 5,241,851 A | 9/1993 | Tapp et al. |
| 5,294,289 A | 3/1994 | Heinz et al. |
| 5,331,409 A | 7/1994 | Thurtell et al. |
| 5,352,902 A | 10/1994 | Aoki |
| 5,453,621 A | 9/1995 | Wong |
| 5,459,574 A | 10/1995 | Lee et al. |
| 5,485,276 A | 1/1996 | Bien et al. |
| 5,517,314 A | 5/1996 | Wallin |
| 5,536,359 A | 7/1996 | Kawada et al. |
| 5,550,636 A | 8/1996 | Hagans et al. |
| 5,561,527 A | 10/1996 | Krone-Schmidt et al. |
| 5,578,829 A | 11/1996 | Talasek et al. |
| 6,154,284 A * | 11/2000 | McAndrew et al. .......... 216/60 |

OTHER PUBLICATIONS

Feher et al., "Tunable Diode Laser Monitoring of Atmospheric Trace Gas Constituents," *Spectrochimica Acta. A 51*, pp. 1579–1599 (1995).

Webster et al, "Infrared Laser Absorption: Theory and Applications," Wiley, New York (1988).

Atkinson, "High Sensitivity Detection of Water Via Intracavity Laser Spectroscopy," *Microcontamination Conference Proceedings*, pp. 98–111 (1994).

Borden, "Monitoring Vacuum Process Equipment: In Situ Monitors—Design and Specification," *Microcontamination*, vol. 9, No. 1, pp. 43–47 (1991).

Grisar et al, "Fast Sampling Devices for Dynamic Exhaust Gas Analysis," *Proceedings of the 24th ISATA International Symposium on Automotive Technology and Automation*, May 20, 1991, pp. 283–287.

Fried, "Versatile Integrated Tunable Diode Laser System for High Precision: Application for Ambient Measurement of OCS," *Applied Optics*, vol. 30, No. 15, May 20, 1991, pp. 1918–1932.

Jasinski et al, "Detection of $SiH_2$ in Silane and Disilane Glow Discharges by Frequency Modulation Absorption Spectroscopy," *Applied Physics Letters*, vol. 44, No. 12, Jun. 15, 1984, pp. 1155–1157.

Pokrowsky et al, "Sensitive Detection of Hydrogen Chloride by Derivative Spectroscopy with a Diode Laser," *Optical Engineering*, vol. 23, No. 1 (1984), pp. 088–091.

Riris et al, "Design of an Open Path Near–Infrared Diode Laser Sensor: Application to Oxygen, Water, and Carbon Dioxide Vapor Detection," *Applied Optics*, vol. 3, No. 30, Oct. 20, 1994, pp. 7059–7066.

May, "Correlation–Based Technique for Automated Tunable Diode Laser Scan Stabilization," *Rev. Sci. Instrum.*, vol. 63, No. 5, May 1992; pp. 2922–2926.

Eng et al, "Tunable Diode Laser Spectroscopy: An Invited Review," *Optical Engineering*, Nov./Dec. 1980, vol. 19, No. 6; pp. 945–960.

Lundqvist et al, "Measurements of Pressure–Broadening Coefficients of NO and $O_3$ Using a Computerized Tunable Diode Laser Spectrometer," *Applied Optics*, vol. 21, No. 17, Sep. 1, 1982; pp. 3109–3113.

Ahlberg et al, "IR–Laser Spectroscopy for Measurement Applications in the Industrial Environment," TR 85170; Dec. 85.

Höjer et al, "Measurements of Electric Field Strength in Gas Insulated High–Voltage Components using Infrared Diode Laser Absorption Spectroscopy," *Applied Optics*, vol. 25, No. 17, Sep. 1, 1986, pp. 2984–2987.

Cassidy, "Trace Gas Detection Using $1.3\mu m$ InGaAsP Diode Laser Transmitter Modules," *Applied Optics*, vol. 27, No. 3, Feb. 1, 1988; pp. 610–614.

Lichtman, "Residual Gas Analysis: Past, Present and Future," *J. Vac. Sci. Technol. A8(3)*, pp. 2810–2813 (1990).

Dreyfus et al, "Optical Diagnostic of Low Pressure Plasmas," *Pure & Appl. Chem.*, vol. 57, No. 9, pp. 1265–1276 (1985).

Davies et al, "Infrared Laser Diagnostics in Methane Chemical–Vapor Deposition Plasmas," *Journal of Applied Physics*, vol. 71, No. 12, Jun. 15, 1992, pp. 6125–6135.

Fried et al, "Application of Tunable Diode Laser Absorption for Trace Stratospheric Measurements of HCL: Laboratory Results," *Applied Optics*, vol. 23, No. 11, Jun. 1, 1984, pp. 1867–1879.

Herriott et al., "Folded Optical Delay Lines", *Applied Optics*, vol. 4, no. 8, pp. 883–889 (8/65).

Inman et al, "Application of Tunable Diode Laser Absorption Spectroscopy to Trace Moisture Measurements in Gases," *Analytical Chemistry*, vol. 66, No. 15, pp. 2471–2479.

May et al, "Data Processing and Calibration for Tunable Diode Laser Harmonic absorption Spectrometers," *J. Quant. Spectrosc. Radiat. Transfer*, vol. 49, No. 4, 1993, pp. 335–347.

May, "Computer Processing of Tunable Diode Laser Spectra," *Applied Spectroscopy*, vol. 43, No. 5, 1989 pp. 834–839.

Mucha et al, "Infrared Diode Laser Determination of Trace Moisture in Gases," *ISA Transactions*, vol. 25, No. 3, pp. 25–30 (1986).

Podolske et al, "Airborne Tunable Diode Laser Spectrometer for Trace–Gas Measurement in the Lower Stratosphere," *Applied Optics*, vol. 32, No. 27, pp. 5324–5333 (1993).

* cited by examiner

SEMICONDUCTOR PROCESSING SYSTEM AND METHOD FOR CONTROLLING MOISTURE LEVEL THEREIN

BACKGROUND OF THE INVENTION

1. Field of the Invention

The present invention relates to a novel semiconductor processing system. The invention also relates to a method for controlling the moisture level in a semiconductor process chamber. The system and method allow for accurate control of the moisture level in a semiconductor processing tool. The invention has particular applicability to the manufacture of semiconductor devices in processes employing water vapor as a process gas.

2. Description of the Related Art

Recently, several dry (i.e., vapor phase) processes employed in the semiconductor manufacturing industry have made use of water vapor as a process gas. The moisture, in the form of water vapor in the process chamber, is typically present in combination with other process gases. Such process include, for example, wet oxidation, copper chemical vapor deposition (Cu-CVD), and photoresist and post-etch residue removal processes.

In such processes, the semiconductor wafers to be treated are introduced into the process chamber of the semiconductor processing tool. The moisture can be introduced into the process chamber in liquid form, where it is subsequently vaporized, or in vapor form, for example, in a carrier gas. Alternatively, the water vapor can be formed in-situ, for example, by reaction of hydrogen ($H_2$) and oxygen ($O_2$) in the process chamber at elevated temperature. In all cases, however, the moisture level in the process chamber is difficult to control as a result of the large influence of adsorption-desorption phenomena taking place in the gas conduits leading up to the process chamber and/or within the process chamber itself.

In light of the foregoing, it has been found that in-situ measurement of moisture levels inside the process chamber can be a very useful tool for process development as well as in mass production to assess run-to-run process reproducibility to help ensure uniformity in semiconductor processing.

Among the analysis tools which can be used in the measurement of water vapor is a type of mass spectrometer, commonly referred to as a residual gas analyzer (RGA). See, e.g., D. Lichtman, Residual Gas Analysis: Past, Present and Future, J. Vac. Sci. Technol., A 8(3) (1990). Mass spectrometers generally require pressures in the range of about $10^{-5}$ torr for operation, whereas the operating pressures of semiconductor processing tools are often higher, for example, in the range of from about 0.1 to 760 torr. Consequently, mass spectrometers require sampling systems and dedicated vacuum pumps, and hence are generally both expensive and not compact in construction. Moreover, the differentially pumped chamber in which the mass spectrometer is housed typically contributes a high level of residual water vapor which is difficult to remove and which severely limits the sensitivity of the mass spectrometer for water vapor measurement.

Optical emission spectroscopy has been widely used for monitoring plasma processes. In principle, optical emission spectroscopy should be useful to monitor the presence of water vapor in the processing tool. However, the optical emission spectrum is very complicated and, furthermore, this method cannot be used in non-plasma processes.

Other spectroscopic techniques have been widely employed in research situations to study process chemistry. See, e.g., Dreyfus et al., Optical Diagnostics of Low Pressure Plasmas, Pure and Applied Chemistry, 57(9), pp. 1265–1276 (1985). However, such techniques generally require specially modified process chambers. For example, the possibility of in-situ moisture monitoring by intracavity laser spectroscopy has been mentioned generally in a review of that technique. See, e.g., G. W. Atkinson, High Sensitivity Detection of Water via Intracavity Laser Spectroscopy, Microcontamination, 94 Proceedings Canon Communications (1994).

Finally, conventional gas analyzers have been applied to in-situ moisture measurement, usually for processes running at or close to atmospheric pressure. See, e.g., Smoak et al., Gas Control Improves Epi Yield, Semiconductor International, pp. 87–92 (June 1990). According to such techniques, a portion of the process gas is extracted into a probe which then delivers the sample to the analyzer. However, use of a probe is undesirable in the measurement of moisture since moisture tends to adsorb on the surfaces of the probe. Moreover, this approach is often impractical as it requires considerable space to accommodate the conventional gas analyzers, which space is typically at a minimum in a semiconductor fabrication cleanroom.

A method for measuring the instantaneous moisture concentration and drydown characteristics of a processing environment is disclosed in U.S. Pat. No. 5,241,851, to Tapp et al. According to this method, a moisture analyzer alternately samples the effluent from a process chamber and the gas generated by a standard gas generator. The output of the standard gas generator is adjusted until the analyzer indicates no difference between the effluent and standard gas streams. Because the moisture content in the output of the standard gas generator is known, the level in the effluent stream can be determined. This system, however, is inconvenient and complicated as it requires a standard gas generator and complicated piping to effect switching between the effluent and standard gas streams. Moreover, there is a risk of backflow from the standard gas generator to the process chamber, resulting in contamination thereof which would be deleterious to the product being formed.

To meet the requirements of the semiconductor processing industry and to overcome the disadvantages of the related art, it is an object of the present invention to provide a semiconductor processing system which allows for monitoring and control of the level of water vapor present as a process gas in an accurate and fast manner.

It is a further object of the invention to provide a method for controlling the moisture level in a semiconductor process chamber which can be practiced on the inventive system.

Other objects and aspects of the present invention will become apparent to one of ordinary skill in the art on a review of the specification, drawings and claims appended hereto.

SUMMARY OF THE INVENTION

According to a first aspect of the invention, novel semiconductor processing systems are provided. The systems comprise a process chamber for treating a semiconductor substrate with one or more process gases comprising water vapor, means for delivering the water vapor or one or more precursors thereof to the process chamber, an exhaust conduit connected to the process chamber, an absorption spectroscopy system for sensing water vapor in a sample region, and a control system which controls water vapor content in the process chamber. The control system comprises a controller responsive to a signal from the absorption spectroscopy measurement system, the controller sending a control signal to the means for delivering the water vapor or precursors thereof.

According to a further aspect of the invention, methods for controlling the moisture level in a semiconductor process chamber are provided. Water vapor or one or more precursors for forming water vapor is introduced to the process chamber. The water vapor is to be employed as a process gas. The water vapor level in a sample region is measured by absorption spectroscopy. The water vapor content in the process chamber is controlled based on the absorption spectroscopy measurement.

BRIEF DESCRIPTION OF THE DRAWINGS

The objects and advantages of the invention will become apparent from the following detailed description of the preferred embodiments thereof in connection with the accompanying drawings, in which like numerals designate like elements, and in which.

DETAILED DESCRIPTION OF THE PREFERRED EMBODIMENTS OF THE INVENTION

The semiconductor processing systems and methods in accordance with the invention will now be described with reference to FIG. 1, which illustrates, in cross-section, a semiconductor processing system 1 in accordance with an exemplary aspect of the invention.

Semiconductor processing system 1 includes a semiconductor process chamber 2, inside which a semiconductor substrate (wafer) 3 is disposed on a substrate holder 4. A single wafer processor is shown merely for purposes of explanation. The invention is also applicable to multiple wafer processors.

One or more gas inlets 5 are provided for delivering a process gas or plural process gases to process chamber 2. To ensure homogenization of the process gases, they are preferably premixed in a mixing manifold 5' prior to introduction to the process chamber 2. Effluent from process chamber 2 is exhausted through an exhaust opening 6 in process chamber 2 and through an exhaust conduit 7.

According to one aspect of the invention, the processing system is suitable to run vacuum processes such as etching and certain chemical vapor deposition processes. In such a case, process chamber 2 can be a vacuum chamber with a vacuum pump 20 connected to the exhaust conduit 7. Alternatively, the processing system can run processes substantially at atmospheric pressure such as atmospheric pressure CVD and thermal oxidation processes, wherein process chamber 2 is held at about atmospheric pressure with a slight vacuum.

Water vapor is included among the process materials which are intended to be present in chamber 2 during processing. The invention therefore finds particular applicability to certain oxidation, chemical vapor deposition (CVD) and dry etching processes which employ water vapor as a process material. More specifically, the invention finds particular applicability to processes including, for example, wet oxidation, Cu-CVD and photoresist and post-etch residue removal processes. These processes may call for reactive or nonreactive (inert) gas species in addition to the water vapor, and the reaction gases can be in a plasma or non-plasma state.

In such processes, the water vapor can be introduced to the process chamber 2 in various ways. For example, the water vapor can be introduced with or without a carrier gas. The water vapor can be generated in a water vapor generating device 15, and then introduced into the gas mixing manifold 5' for mixing with the other process gases prior to introduction into the process chamber 2. The water vapor can be introduced directly into the process chamber 2.

The desired water content in the process may vary, including periods of no desired water content, depending on the specific process. In some cases it may be advantageous to have water vapor only during certain process steps, or different levels in different process steps.

Figure 2A:
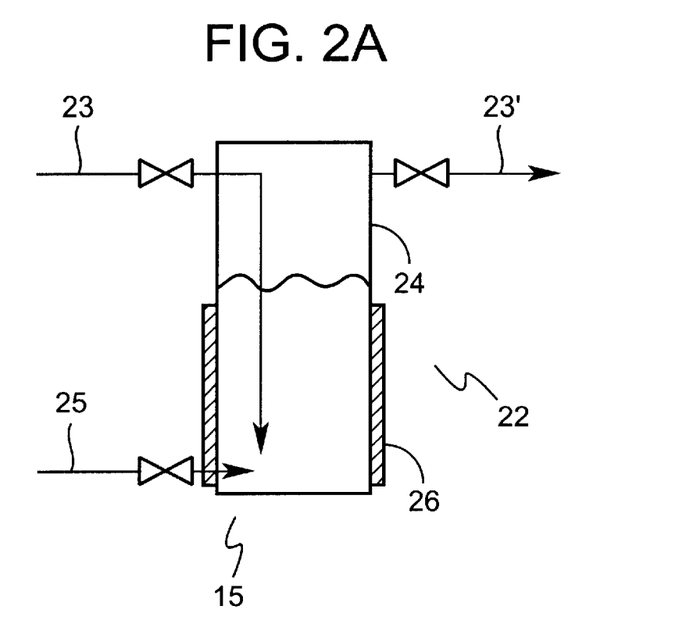
FIGS. 2A and 2B are diagrams of exemplary moisture generators which can be used in the semiconductor processing systems and methods in accordance with the invention.

With reference to FIG. 2A, the water vapor generating device can be, for example, a bubbler or vaporizer 22. A carrier gas is introduced through a conduit 23 into vessel 24, and the gas is bubbled through the water contained therein. The moisture-containing carrier gas is removed from the bubbler through conduit 23'. Water vapor concentration is a function of the carrier gas contact time in the water, together with temperature and pressure. As the vapor is extracted from the vessel, the liquid level in vessel 24 decreases and fresh water can be introduced through conduit 25. The temperature of the water in the vessel 24 can be controlled by an external heater 26.

Figure 2B:
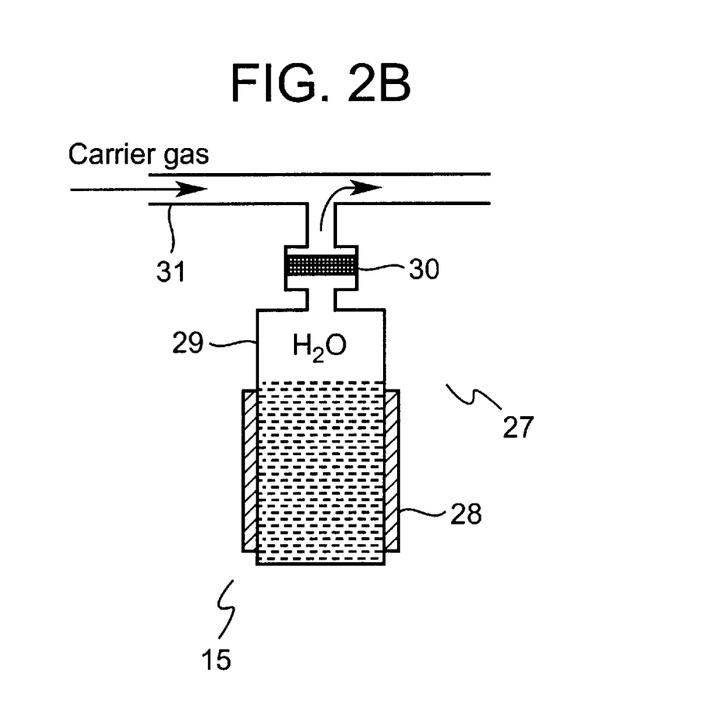

With reference to FIG. 2B, the water vapor generating device can optionally be one or more heated permeation tubes 27, the temperature of which can be controlled by a heater 28. The permeation tube 27 includes a cartridge 29 containing liquid water. The cartridge 29 is typically sealed with a polymeric material 30 through which the moisture diffuses. A carrier gas flows through conduit 31, thus sweeping the polymer surface, and becomes moist. The concentration of moisture in the carrier gas is inversely proportional to the carrier gas flow rate, and increases with the cartridge temperature.

It is further possible to directly introduce liquid water into process chamber 2, wherein it becomes vaporized at elevated temperature. In such a case, a liquid mass flow controller can be used for flow control into the chamber.

As an additional alternative, the water vapor can be generated in-situ in process chamber 2 from starting materials (precursors) which include oxygen and hydrogen gases introduced into process chamber 2 via separate conduits.

Flow of these materials into the chamber can be controlled by mass flow controllers on each conduit.

The specific method of introduction of the water vapor into the chamber will depend in part on the process being run. For example, in the case of Cu-CVD, water vapor may be added to a feed stream containing the copper precursor, while in photoresist and post-etch residue removal processes, it may be desired to introduce the water vapor into the process chamber in the form of moist ozone ($O_3$). In-situ generation may be desirable in the wet oxidation process by introduction of oxygen and hydrogen into the oxidation chamber.

1. Principles of Operation of Measurement System

When light is absorbed by molecules in the path of light of frequency ν, the measured absorbence can be converted into the partial pressure of the species of interest according to Beer's Law, according to the following equation:

$$T(v) = \frac{I(v)}{I_0(v)} = \exp(-\alpha(v)cl)$$

or, in the case of small absorptions, according to the following equation:

$$\frac{I_0(v) - I(v)}{I_0(v)} \approx \alpha(v)cl$$

In the above equations, T(ν) is the transmittance at frequency ν, i(ν) is the light intensity measured at the detector after passing through the sample cell, $I_0(v)$ is the light intensity in the absence of absorption, α(ν) is the absorption coefficient at frequency ν, c is the concentration of the absorbing species and l is the pathlength. The absorption coefficient a is typically stated in terms of a lineshape function (ν) and an intensity factor S, according to the following equation:

$$\alpha(v) = S\kappa(v)$$

wherein κ has the well-known Gaussian, Lorentzian or Voigt form.

To eliminate low frequency noise sources, the sensor to preferably uses wavelength modulation spectroscopy with second harmonic detection. The laser output is modulated at a frequency f with a modulation amplitude m, according to the following equation:

$$v \rightarrow v + m\cos(2\pi ft) = v + m\cos\theta$$

The detector signal is demodulated to obtain the component in phase with 2 f. The demodulated signal ($V_2$) is proportional to the 2 f term in the Fourier expansion of α(ν), shown as the following equation:

$$V_2 = CI_0 Scl \int_{-\pi}^{\pi} \kappa(v + m\cos\theta)\cos(2\theta) d\theta$$

wherein S and κ(ν) are available for the water vapor absorption spectrum over the pressure and temperature range usually found in the exhaust conduits of semiconductor process tools. The integral is evaluated numerically assuming a Voigt profile. The proportionality constant C is determined by the response of the detector and signal processing electronics. In principle, C may be evaluated from first principles, but it is more practical to measure $V_2/I_0$ for known c, l, κ(ν) and m, and hence deduce C. It is important to verify that the signal-processing electronics response produces a response that varies linearly with water vapor concentration and to repeat the calibration periodically to ensure that no significant drift in the electronics response occurs over time. It is believed that a calibration of one time per year will be sufficient.

2. Measurement System Components

Figure 1:
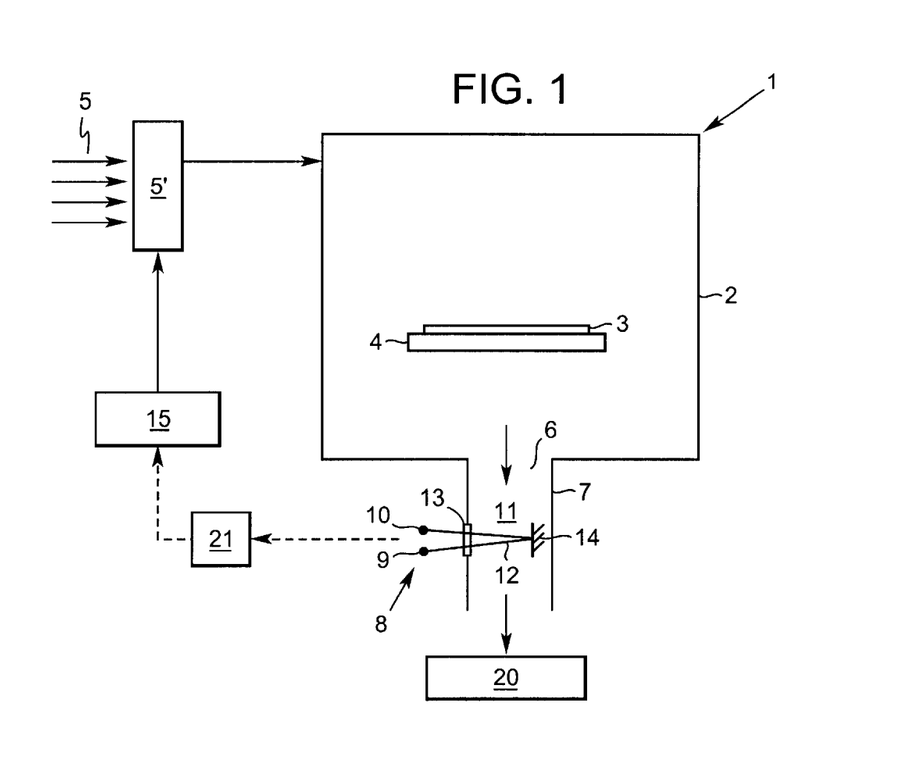
FIG. 1 is a cross-sectional view of a semiconductor processing system in accordance with an exemplary aspect of the invention.
Figure 3:
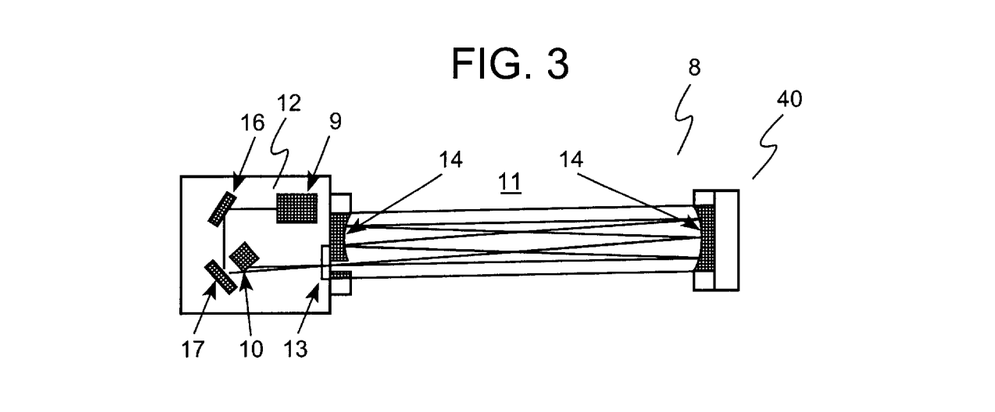
FIG. 3 is a plan view of an exemplary absorption spectroscopy measurement system which can be used in the semiconductor processing system of the invention.

With reference to FIGS. 1 and 3, the semiconductor processing system includes an absorption spectroscopy measurement system 8 to detect and measure the concentration of water vapor in the processing tool. A suitable measurement system is commercially available from SOPRA SA, Bois Colombes, France, and is described in one or more of U.S. Pat. Nos. 5,742,399, 5,818,578, 5,835,230, 5,880,850, 5,949,537, 5,963,336, 5,991,696 and 6,084,668, the contents of which documents are herein incorporated by reference.

The absorption spectroscopy measurement system 8 comprises a light source 9 and a detector 10, which can be a photodiode, in optical communication with a sample region 11. In this exemplary embodiment, the sample region is located in process chamber exhaust conduit 7. The sample region can, however, be disposed at positions other than the exhaust conduit such as upstream from the process chamber. This allows sampling of the gases being introduced into the process chamber. Additionally, the sample region can be inside the process chamber itself or at other positions downstream of the process chamber, such as where a sample portion of the exhaust is analyzed.

In order to detect water vapor, it is important that a light source which emits light of a wavelength characteristic thereof is employed. Laser light sources which emit light in spectral regions where the water vapor molecules absorb most strongly lead to improvements in measurement sensitivity.

Any suitable wavelength-tunable light source can be used. Of the currently available light sources, diode laser light sources are preferred because of their narrow linewidth (less than about $10^3$ cm$^{-1}$) and relatively high intensity (about 0.1 to several milliwatts) at the emission wavelength. The diode is preferably of the distributed feedback (DFB) type, ensuring single mode emission, i.e., to ensure that the diode emits at a single frequency, as described in M. Feher et al, Spectrochimica Acta A 51 pp. 1579–1599 (1995). In accordance with a preferred aspect of the invention, an InGaAsP/InP Distributed Feedback (DFB) diode laser operating at about 1.368 μm is employed as the light source 9 in order to use the strongest absorption lines for $H_2O$ in the near infrared.

Suitable light sources for use in the invention are not, however, limited to diode lasers. For example, other types of lasers which are similarly sized and tunable by simple electrical means, such as fiber lasers and quantum cascade lasers, can be employed. The use of such lasers as they become commercially available is envisioned.

Light source electronics control the current applied to the diode laser or other light source such that it emits light of a specific wavelength which is absorbed by the water vapor. As current applied to the laser diode increases, wavelength increases or decreases depending on the diode type. Laser current controllers are known in the art and are commercially available, for example, the ILX Lightwave LDX-3620.

Light beam 12 which is generated by the described light source 9 is transmitted into the sample region 11 through at least one light transmissive window 13. The measurement system can be configured such that light beam 12 is reflected by one or more light reflective surfaces 14 within the sample region and exits sample region 11 through the same window 13 it enters the sample region through. Alternatively, the windows through which the light beam enters and exits the sample region can be different and can be disposed on different sides of the sample region 11. The measurement system can also be configured such that the light beam passes straight through the sample region from a light inlet window through a light exit window without being reflected in the sample region.

Light reflective surface 14 can be formed either separate from or integral with a wall defining the sample region. Light reflective surface 14 is preferably a polished metal. As a high reflectivity of this surface is desirable, the surface can be coated with one or more layers of a reflective material such as gold, other metallic layers or a highly reflective dielectric coating in order to enhance the reflectivity thereof. Moreover, to minimize the adverse effects created by deposits formed on the light reflective surfaces, a heater for heating the light reflective surface can also be provided.

FIG. 3 illustrates an exemplary absorption spectroscopy measurement system 8 which can be used with the invention. As shown, a measurement cell 40 includes a plurality of mirrors (or one mirror having multiple faces) can be disposed within the exhaust conduit 7 (or process chamber 2), thereby forming a multipass cell. This allows the light beam to pass through the sample region a plurality of times. By increasing the effective pathlength in this manner, sensitivity of the measurement system is thereby enhanced. Such a cell can have a path length, for example, of up to 17 meters. Of the various multipass designs, the cell used in the present invention is preferably of the Herriott type, as illustrated.

The absorption spectroscopy measurement system 8 can further include first and second mirrors 16, 17 for reflecting light beam 12 from light source 9 through light transmissive window 13 into the sample region. Other mirror schemes for manipulating the light beam are envisioned. Mirrors 16, 17 as shown are flat, but can alternatively be curved if it desired to collimate the light beam.

A detector 10, such as a photodiode, responds to light of the same wavelength as emitted by the diode laser. Detector 10 responds to light beam 12 which exits the sample region through light transmissive window 13. Detector 10 is preferably an InGaAs photodiode. Suitable detectors are commercially available, for example, the EG&G InGaAs C30641 for near infrared detection, with a 10-MHZ bandwidth amplifier.

Detector electronics receive the output from the detector and generate an output which is related to the absorbence of light at the desired wavelength. The absorbence (A) is defined as $A=1-T$, wherein T is the transmittance, i.e., the ratio of the detected light intensity in the presence of the water vapor measured to the intensity which would be observed in its absence. The absorbance can be converted into a concentration of the molecular impurities by a computer using known calibration data.

Various methods for controlling the wavelength of the light emitted by the diode laser can be used. For example, the laser wavelength may be locked to the desired value by a feedback system. Alternatively, it may be rapidly and repetitively swept by modulating the diode current with a sawtooth function over a region which includes the desired wavelength of the moisture absorption line to generate a spectrum. The region is selected to be free of interference from other species used or formed in the process. Subsequent spectra may be averaged to improve sensitivity. Both of these techniques are known. See, e.g., Feher et al., *Tunable Diode Laser Monitoring of Atmospheric Trace Gas Constituents, Spectrochimica Acta,* A 51, pp. 1579–1599 (1995) and Webster et al., Infrared Laser Absorption: Theory and Applications, Laser Remote Chemical Analysis, R. M. Measuews (Ed.), Wiley, New York (1988).

Further improvements in sensitivity can be achieved by modulating the diode current and wavelength and demodulating the detector signal at the modulation frequency or one of its higher harmonics. This technique is known as harmonic detection spectroscopy. See, Feher et al., *Tunable Diode Laser Monitoring of Atmospheric Trace Gas Constituents, Spectrochimica Acta,* A 51, pp. 1579–1599 (1995) and Webster et al., Infrared Laser Absorption: Theory and Applications in Laser Remote Chemical Analysis, R. M. Measuews (Ed.), Wiley, New York (1988).

Suitable signal demodulation and numerical data treatment makes measurements of the moisture partial pressure feasible with a sampling rate of up to 0.5 Hz. In addition, the sensor requires in principle no calibration since it is based on the absorption of incident laser light, which depends solely on the moisture concentration, the optical pathlength, the gas pressure and molecular parameters (e.g., oscillator strength).

Figure 4:
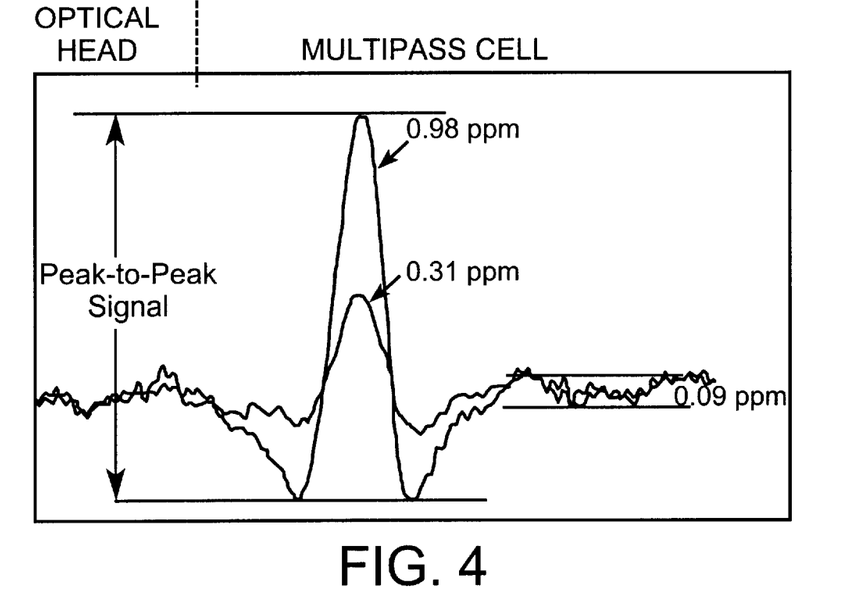
FIG. 4 is an infrared spectrum generated by the semiconductor processing system in accordance with the invention.

In accordance with an exemplary embodiment of the invention, the laser wavelength is modulated, for example, at 10 Hz, using a repetitive current ramp which scans over the wavelength range where water vapor absorbs the incident light. A second modulation at 128 kHz is also applied to the diode and phase-sensitive detection is used to select the component of the detector signal which is in phase with the second harmonic of the modulation signal (256 kHz), as described above. This results in a spectrum as shown in FIG. 4.

Software locates the minimum and the maximum signal values during the scan. The difference between these is referred to as the "peak-to-peak" signal or "pp2f." The absolute value of the light intensity is determined from the DC component of the detector signal corresponding to the absorption peak. Interpolation of the DC signal trace on either side of the peak is used to correct for the change in light intensity due to absorption.

A matrix of pp2f values is precalculated by evaluating Equation (2) above, for a range of pressures and temperatures and the chosen value of the modulation amplitude m. This is loaded into memory when the sensor is initialized. The observed pp2f value is converted into absorbence using the matrix, the light intensity and a constant factor that accounts for the gain of the electronics. The absorbence is then converted to moisture concentration according to Beer's Law using Equation (1).

A monitor can be connected directly, to provide a real-time display of the moisture concentration along with some key parameters such as the system pressure, laser power, etc. A D/A converter is used to provide a 0–5V analog output proportional to the moisture signal, as well as alarm signals as required.

The system continuously records data for moisture as a function of time. The data can periodically be saved, for example, to an ASCII file, on a memory device such as a removable hard drive. It has been found that saving the data every twenty minutes, with a data point being collected every two seconds, is sufficient.

3. Control of Moisture Level

In accordance with the present invention, a signal corresponding to the measured water vapor level in the sample region 11 is used to control a moisture introduction system such that the moisture level can be controlled in a desired manner. A control signal from the absorption spectroscopy measurement system 8 is sent to a controller 21 which, in turn, sends a control signal to the water vapor generating device 15. The controller 21 can take various forms known to persons skilled in the art, but is preferably a programmable logic controller (PLC) or other type of logic controller.

A moisture set-point at the selected exhaust or other measurement location can be defined at first. Once the moisture set-point has been established at a given point, a feedback control loop technique (e.g., proportional-integral-derivative) can be implemented with the controller and moisture generator. In this way, the output of the moisture generator 15 can be controlled by adjustment of a control variable of the moisture generator. The control variable can be, for example, temperature, carrier gas flow rate, or gas or liquid flow rate, depending on the particular type of moisture generator employed.

The manner of controlling the moisture level will depend on the nature of the water vapor generation. For example, in the case of moisture addition via a water vapor stream with or without a carrier gas, controller 21 can send a control signal to a mass flow controller which adjusts the total moisture flow into the chamber. Similarly, in the case of direct liquid water injection into the chamber, a liquid mass flow controller can be controlled based on the moisture measurement.

Where a bubbler or vaporizer containing water is employed for moisture introduction, controller 21 sends a control signal to heater 26 to control the temperature of the water in the vessel 24. Additionally or alternatively, the flow rate of the carrier gas, if any, introduced into the bubbler or vaporizer through conduit 23 can be controlled.

Where temperature sensitive permeation tubes 27 are employed for water vapor introduction, the signal from controller 21 can be used to control the temperature of the permeation tubes via heater 28 in a similar manner to that described above, and/or flow rate of the carrier gas in conduit 30 can be controlled.

Figure 5:
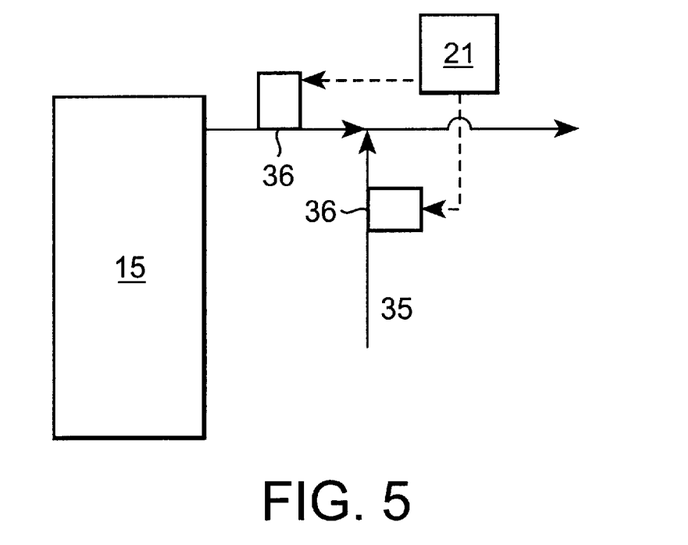
FIG. 5 is a diagram of an exemplary moisture dilution scheme in accordance with the invention.

To allow for improved response times in moisture content adjustment, a moisture dilution scheme can be used. FIG. 5 illustrates an exemplary scheme for doing so. One or more dilution gas streams 35 are provided to adjust the moisture concentration in the outlet from moisture generator 15. Mass flow controllers 36 on the moisture generator outlet line and/or the dilution gas stream line(s) 35 are provided to control flow of the moisture-containing gas flow stream and/or the dilution gas stream(s), based on the signal from controller 21.

The moisture content in the final stream can thereby be controlled by varying the relative flows of the moisture-containing stream and the dilution gas stream(s). The dilution gas stream can be an inert gas, preferably the same type of gas as the carrier gas in the moisture-containing stream. Other or additional types of gases can be used. For example, the dilution gas can contain one or more of the process gases, e.g., a reactive gas, employed in the process. The dilution gas should have a low moisture content compared to that in the moisture-containing stream.

U.S. Pat. Nos. 5,635,620, 5,587,519, 5,937,886, 5,928,415, 5,922,286 and 5,900,214, the entire contents of which documents are incorporated herein by reference, describe various techniques for mixing and delivering gases to an apparatus. The configuration of the above-described moisture dilution scheme can be further modified based on these documents to further improve response time.

For in-situ moisture generation, for example, by reaction of hydrogen and oxygen, the system can control the flow rate of either or both of the reactants by controlling mass flow controllers on the conduits. Preferably, the flow rate of the reactant which limits the reaction, e.g., hydrogen when oxygen is in excess, is controlled. Optionally, controller 21 can be used to control a physical variable such as reaction temperature via a process chamber heater to control the water vapor formed as a result of the reaction.

Figure 6:
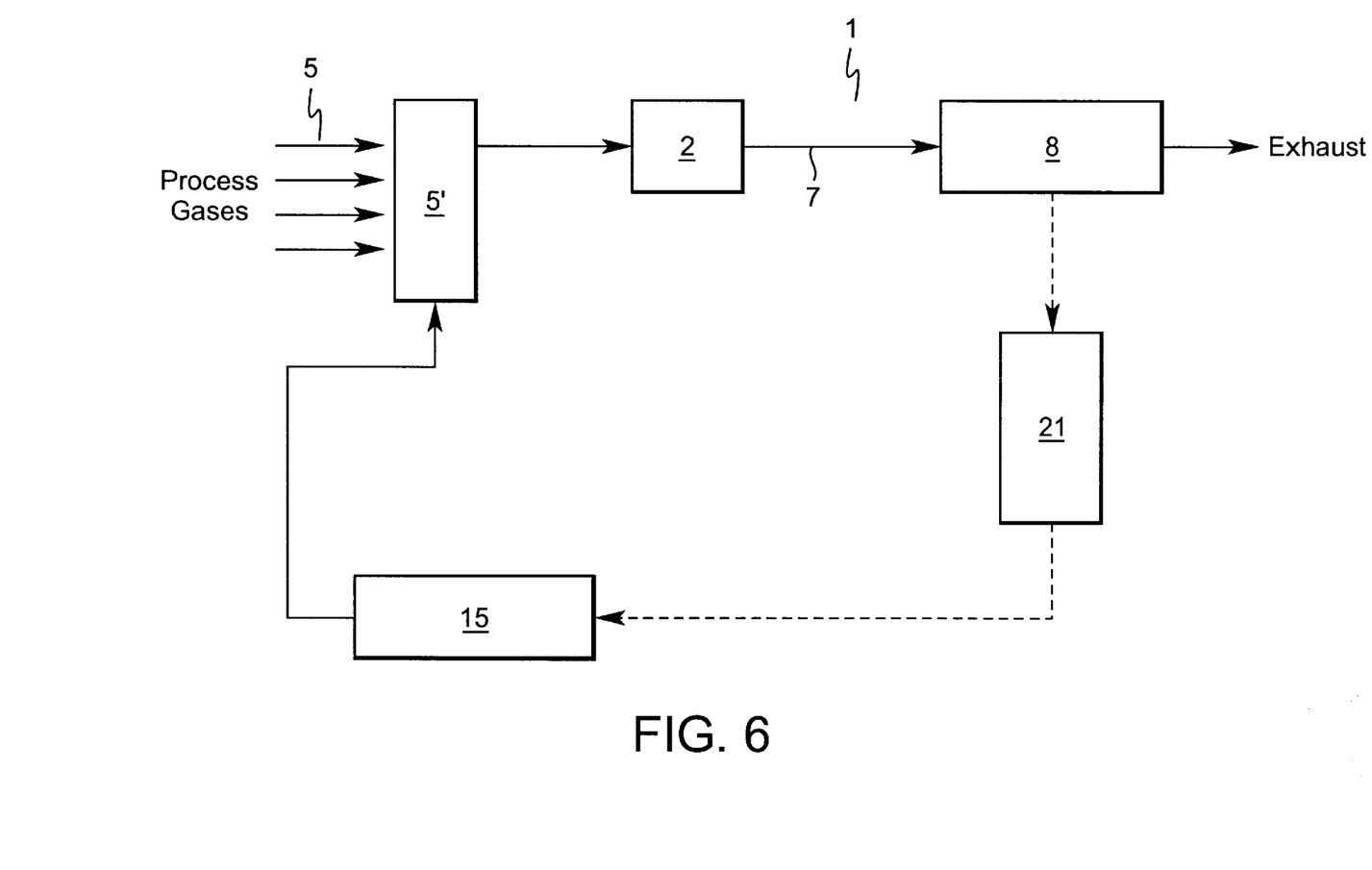
FIG. 6 is a schematic diagram of an exemplary semiconductor processing system in accordance with the invention.

A schematic diagram illustrating a first exemplary embodiment of the invention is shown in FIG. 6. In this configuration, the sample region is in the process chamber exhaust conduit 7. The sensor 8 is connected to the exhaust conduit 7 from the process chamber 2, for example, in the manner illustrated in FIG. 1. The sensor provides a signal indicative of the moisture level in the sample region to the controller 21 which, in turn, sends a control signal to the moisture generating device 15. Moisture is added directly to the process gases in the gas mixing manifold 5' with or without a carrier gas by the moisture generating device 15 based upon such signal.

The process gases in gas conduits 5 can advantageously be premixed in gas mixing manifold 5' prior to entering the process chamber 2. Premixing of the process gases advantageously ensures a homogeneous reaction mixture resulting in more uniform processing.

In this embodiment, because the moisture sensor 8 monitors the moisture level in the gases exiting the process chamber 2, the potential for contamination of the process in chamber 2 by the sensor can be avoided. Additionally, retrofitting of existing equipment can be achieved without modifying existing gas piping and controls leading to the inlet of the process chamber.

The chemistry of the process being conducted in process chamber 2 may lead to the generation or consumption of moisture during the course of the process. As a result, moisture sensor measurement of the exhaust gas or at selected points within the process chamber may not provide a direct indication of the moisture being added to the system.

Figure 7:
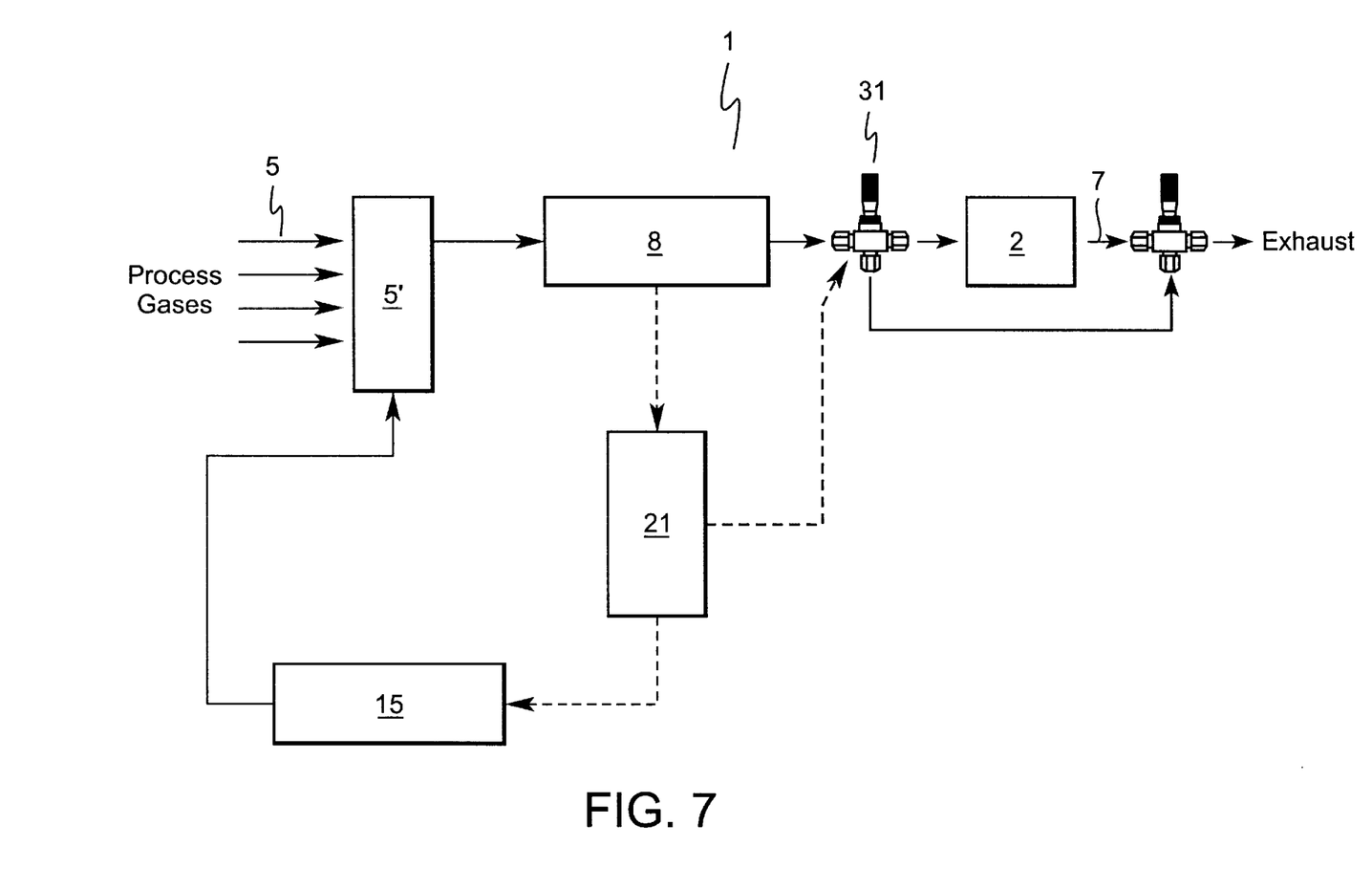
FIG. 7 is a schematic diagram of a further exemplary semiconductor processing system in accordance with the invention.

FIG. 7 is a schematic diagram illustrating a semiconductor processing system in accordance with a further aspect of the invention which addresses such problem. This embodiment allows for direct measurement of the moisture level in the gas mixture being introduced into the process chamber 2.

The process gas mixture from mixing manifold 5' is passed through a sample region of moisture sensor 8 prior to introduction into the process chamber 2. A signal indicative of the moisture level in the gas mixture is sent to the controller 21 by sensor 8. By use of a control strategy (e.g., proportional-integral-derivative) as described above, the output of the moisture generator 15 can be appropriately controlled. The water vapor with or without carrier gas, or water vapor precursor, is introduced into mixing manifold 5' or into process chamber 8 directly.

Optionally, a bypass valve 31 can be employed downstream of the moisture sensor 8 and upstream of the process chamber 2. When opened, the bypass valve allows the gas mixture to enter the process chamber 2 and, when closed, directs the gas mixture directly to exhaust. If the moisture content of the gas mixture is of a predetermined level or range, the bypass valve is opened and the gas is directed to the process chamber 2. Otherwise, the bypass valve is closed, directing the gas mixture to exhaust. In this way, the moisture concentration in the homogeneous reaction mixture can be stabilized prior to initiating the process in chamber 2.

A preferred method in accordance with this aspect of the invention involves introducing a semiconductor substrate into the process chamber 2. Flow of the process gases at their respective set points is initiated with the process bypass valve 31 in the closed (i.e., process chamber bypass) position. The moisture concentration of the homogeneous gas mixture is continuously measured and controlled by the moisture sensor to a predetermined level or range. When the moisture concentration is within specification and, optionally, after a predetermined period of time has lapsed at such condition, the process bypass valve 31 is opened. The homogeneous reaction mixture is thus allowed to flow into the process chamber 2. The semiconductor process is then started, optionally, with continued monitoring and control by the moisture sensor.

Figure 8:
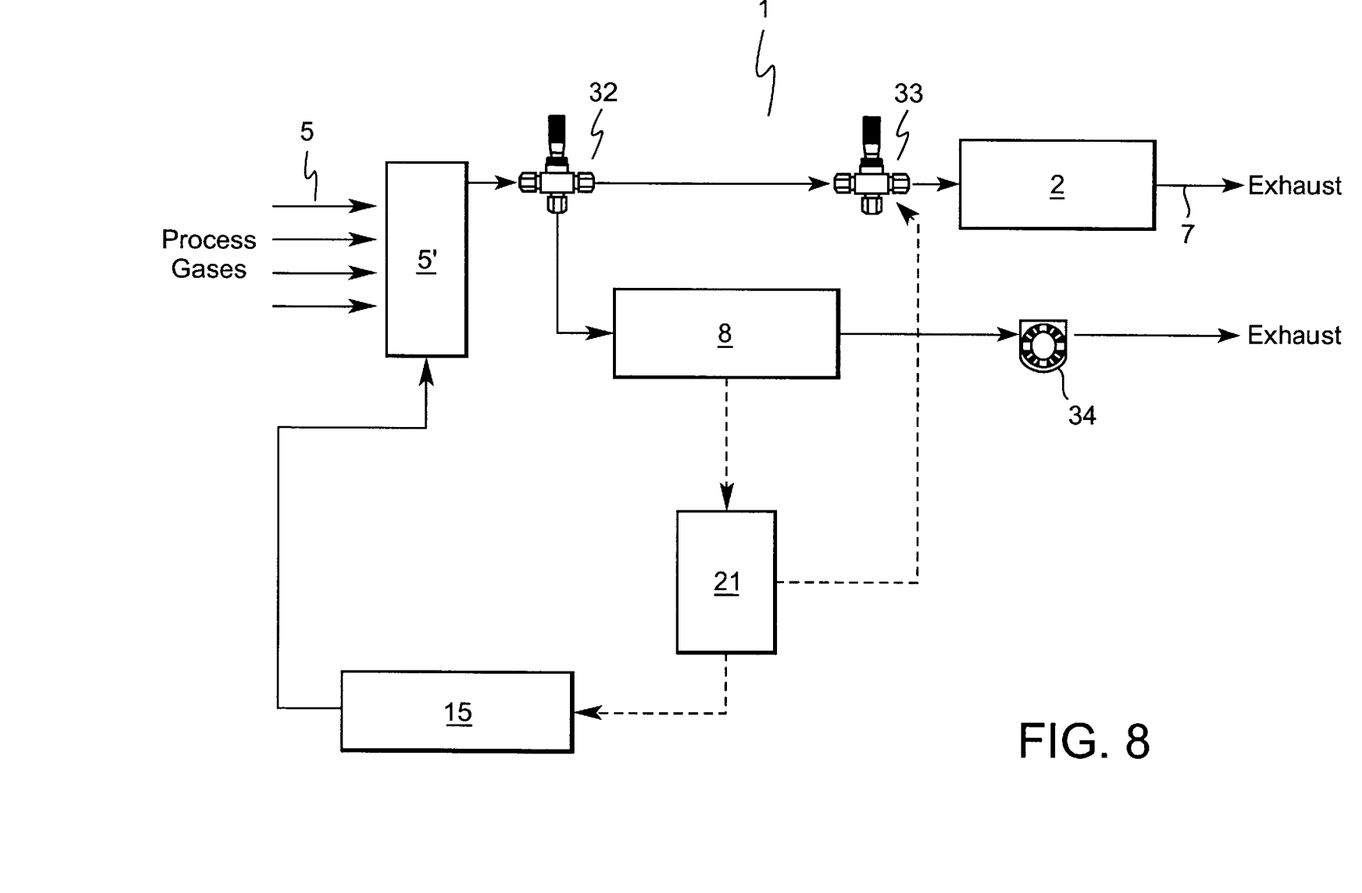
FIG. 8 is a schematic diagram of a further exemplary semiconductor processing system in accordance with the invention.

A further exemplary embodiment of the invention is illustrated in FIG. 8. In this configuration, after mixing of the process gases in mixing manifold 5', the process gas mixture is divided into two portions by valve 32. A first, sample portion of the process gas mixture passes through valve 32 and continuously flows through the moisture sensor 8 for moisture level analysis. This first portion is pulled through the system by pump 34, and is removed as exhaust. A second, process gas portion of the gas mixture passes through valve 32 and is introduced into the process chamber 2 when valve 33 is in the open position. Valve 33 is normally closed, but opens after the moisture level of the gas mixture as measured by sensor 8 attains a predetermined moisture level or range. The flow rate through the moisture sensor 8 is controlled independently of the total gas flow to the process chamber 2. The total gas supplied to the mixing manifold 5' should therefore satisfy the flow requirements of both the moisture sensor and process.

A preferred method in accordance with this aspect of the invention involves introducing a semiconductor substrate into the process chamber 2. Flow of the process gases at their respective set points is initiated with valve 33 in the closed position. The moisture concentration of the homogeneous gas mixture is continuously measured by the moisture sensor 8, and is controlled to a predetermined level or range by controller 21 and moisture generating device 15 in the manner described above. When the moisture concentration is within specification and, optionally, after a predetermined period of time has lapsed at such condition, a control signal is sent to valve 33 which is opened, allowing the homogeneous reaction mixture to flow into the process chamber 2. The semiconductor process is then started, optionally, with continued monitoring and control by the moisture sensor.

This configuration allows for a stable moisture concentration in the reaction gas mixture prior to delivery to the process chamber 2 by use of an appropriate control loop as described above. This embodiment further ensures that the gases introduced into the process chamber do not pass through the moisture sensor. Potential contamination of the process resulting from the moisture sensor is thereby eliminated. Additionally, because the moisture sensor in this configuration is not an integral part of the gas system supplying the process chamber, it is possible to disconnect the sensor in case of malfunction thereof without taking the process chamber out of service.

While the invention has been described in detail with reference to specific embodiments thereof, it will be apparent to one skilled in the art that various changes and modifications can be made, and equivalents employed, without departing from the scope of the appended claims.

What is claimed is:

1. A semiconductor processing system, comprising:
    a process chamber for treating a semiconductor substrate with one or more process gases comprising water vapor;
    means for delivering the water vapor or one or more precursors thereof to the process chamber;
    an exhaust conduit connected to the process chamber;
    an absorption spectroscopy system for sensing water vapor in a sample region; and
    a control system which controls water vapor content in the process chamber, the control system comprising a controller responsive to a signal from the absorption spectroscopy measurement system and sending a control signal to the means for delivering the water vapor or precursors thereof.

2. The semiconductor processing system according to claim 1, wherein the sample region is downstream of the process chamber.

3. The semiconductor processing system according to claim 1, further comprising a gas mixing manifold upstream of the process chamber for premixing one or more process gases other than the water vapor with the water vapor or precursors thereof.

4. The semiconductor processing system according to claim 3, wherein the sample region is downstream of the process chamber.

5. The semiconductor processing system according to claim 3, wherein the sample region is downstream of the gas mixing manifold and upstream of the process chamber.

6. The semiconductor processing system according to claim 5, further comprising a valve downstream of the sample region and upstream of the process chamber, the valve being controlled based on the control signal from the controller to allow the gas from the sample region to pass into the process chamber.

7. The semiconductor processing system according to claim 3, wherein the sample region is downstream of the gas mixing manifold and in parallel with the process chamber.

8. The semiconductor processing system according to claim 7, further comprising a valve downstream of the mixing manifold and upstream of the process chamber, the valve being controlled based on the control signal from the controller to allow the gas from the mixing manifold to pass into the process chamber.

9. The semiconductor processing system according to claim 1, wherein the means for delivering the water vapor or precursors thereof comprises a bubbler, the bubbler comprising a vessel containing liquid water and a carrier gas inlet for bubbling a carrier gas into the water.

10. The semiconductor processing system according to claim 9, wherein the bubbler further comprises a heater controlled based on the control signal from the controller.

11. The semiconductor processing system according to claim 9, further comprising a flow control device on the carrier gas inlet, the flow control device being controlled based on the control signal from the controller.

12. The semiconductor processing system according to claim 1, wherein the means for delivering the water vapor or precursors thereof comprises one or more temperature sensitive permeation tubes connected to a carrier gas conduit.

13. The semiconductor processing system according to claim 12, wherein the one or more temperature sensitive permeation tubes comprise a heater controlled based on the control signal from the controller.

14. The semiconductor processing system according to claim 12, further comprising a flow control device on the carrier gas conduit, the flow control device being controlled based on the control signal from the controller.

15. The semiconductor processing system according to claim 1, wherein the means for delivering the water vapor or precursors thereof comprises an oxygen conduit connected to an oxygen source and a hydrogen conduit connected to a hydrogen source.

16. The semiconductor processing system according to claim 1, wherein the means for delivering the water vapor or precursors thereof comprises a liquid water conduit connected to a liquid water source.

17. The semiconductor processing system according to claim 1, wherein the process chamber forms part of an oxidation system, an etching system or a chemical vapor deposition system.

18. The semiconductor processing system according to claim 17, wherein the process chamber forms part of a copper chemical vapor deposition system.

19. The semiconductor processing system according to claim 1, wherein the means for delivering the water vapor or precursors thereof comprises a first conduit connected to receive a gas comprising water vapor, a second conduit connected to receive a dilution gas, the first and second conduits being connected to combine the gas comprising water vapor with the dilution gas, a third conduit connected to the process chamber to deliver the combined gas thereto, a flow control device connected to the first conduit and/or a flow control device connected to the second conduit, the flow control device(s) being responsive to the control signal from the controller.

20. A method for controlling the water vapor level in a semiconductor process chamber, comprising the steps of:

introducing water vapor or one or more precursors for forming water vapor to the process chamber, wherein the water vapor is to be employed as a process gas;

measuring the water vapor level in a sample region by absorption spectroscopy; and controlling the water vapor content in the process chamber based on the absorption spectroscopy measurement.

21. The method according to claim 20, wherein the sample region is downstream of the process chamber.

22. The method according to claim 20, further comprising premixing one or more process gases other than the water vapor with the water vapor or precursors thereof upstream of the process chamber.

23. The method according to claim 22, wherein the sample region is downstream of the process chamber.

24. The method according to claim 22, wherein the sample region is downstream of the premixing point and upstream of the process chamber.

25. The method according to claim 24, further comprising controlling a valve disposed downstream of the sample region and upstream of the process chamber based on the absorption spectroscopy measurement to allow the gas from the sample region to pass into the process chamber.

26. The method according to claim 22, wherein the sample region is downstream of the premixing point and in parallel with the process chamber.

27. The method according to claim 26, further comprising controlling a valve disposed downstream of the premixing point and upstream of the process chamber based on the absorption spectroscopy measurement to allow the gas from the premixing point to pass into the process chamber.

28. The method according to claim 20, wherein the water vapor is generated by bubbling a carrier gas through water in a bubbler.

29. The method according to claim 28, further comprising controlling the temperature in the bubbler based on the absorption spectroscopy measurement.

30. The method according to claim 28, further comprising controlling flow rate of the carrier gas based on the absorption spectroscopy measurement.

31. The method according to claim 20, wherein the water vapor is generated by passing a carrier gas over one or more temperature sensitive permeation tubes.

32. The method according to claim 31, further comprising controlling the temperature of the one or more temperature sensitive permeation tubes based on the absorption spectroscopy measurement.

33. The method according to claim 31, further comprising controlling the a flow rate of the carrier gas based on the absorption spectroscopy measurement.

34. The method according to claim 20, wherein the one or more precursors for forming water vapor comprise oxygen and hydrogen.

35. The method according to claim 20, wherein the water vapor is generated by introducing liquid water into the process chamber and heating the liquid water.

36. The method according to claim 20, wherein the process chamber forms part of an oxidation system, an etching system or a chemical vapor deposition system.

37. The method according to claim 36, wherein the process chamber forms part of a copper chemical vapor deposition system.

38. The method according to claim 20, wherein the water vapor content is controlled prior to introduction into the process chamber by adding a dilution gas stream to a gas stream comprising the water vapor, and adjusting the flow rate of the dilution gas stream and/or the water vapor-comprising stream, thereby forming a combined gas stream having a desired water vapor content, wherein the combined gas stream is introduced into the process chamber.

* * * * *